(12) United States Patent
Dubson et al.

(10) Patent No.: US 7,115,220 B2
(45) Date of Patent: Oct. 3, 2006

(54) VASCULAR PROSTHESIS AND METHOD FOR PRODUCTION THEREOF

(75) Inventors: Alexander Dubson, Hadera (IL); Eli Bar, Moshav Megadim (IL)

(73) Assignee: Nicast Ltd., Lod (IL)

( * ) Notice: Subject to any disclaimer, the term of this patent is extended or adjusted under 35 U.S.C. 154(b) by 25 days.

(21) Appl. No.: 10/433,622

(22) PCT Filed: Dec. 17, 2001

(86) PCT No.: PCT/IL01/01172

§ 371 (c)(1),
(2), (4) Date: Jun. 18, 2003

(87) PCT Pub. No.: WO02/49536

PCT Pub. Date: Jun. 27, 2002

(65) Prior Publication Data

US 2004/0054406 A1 Mar. 18, 2004

Related U.S. Application Data

(60) Provisional application No. 60/276,956, filed on Mar. 20, 2001, provisional application No. 60/256,323, filed on Dec. 19, 2000.

(51) Int. Cl.
*B29C 47/06* (2006.01)

(52) U.S. Cl. .............................. 264/6; 264/413; 264/10; 264/440; 425/174.8 E

(58) Field of Classification Search ........ 264/437–441, 264/6, 10, 413, 465; 425/174.8 E
See application file for complete search history.

(56) References Cited

U.S. PATENT DOCUMENTS

| 2,491,889 | A | | 12/1949 | Bennett et al. |
|---|---|---|---|---|
| 3,280,229 | A | | 10/1966 | Simons |
| 3,425,418 | A | | 2/1969 | Chvapil et al. |
| 3,625,745 | A | | 12/1971 | Wright et al. |
| 3,688,317 | A | | 9/1972 | Kurtz |
| 3,860,369 | A | | 1/1975 | Brethauer et al. |
| 4,044,404 | A | | 8/1977 | Martin et al. |
| 4,223,101 | A | | 9/1980 | Fine et al. |
| 4,323,525 | A | | 4/1982 | Bornat |
| 4,345,414 | A | | 8/1982 | Bornat et al. |
| 4,368,277 | A | | 1/1983 | Burinsky et al. |
| 4,524,036 | A | * | 6/1985 | Gilding et al. ................ 264/10 |
| 4,657,793 | A | | 4/1987 | Fisher |
| 4,689,186 | A | * | 8/1987 | Bornat ......................... 264/6 |
| 4,738,740 | A | * | 4/1988 | Pinchuk et al. ............. 156/167 |
| 4,739,013 | A | | 4/1988 | Pinchuk |
| 4,743,252 | A | | 5/1988 | Martin, Jr. et al. |
| 4,759,757 | A | | 7/1988 | Pinchuk |

(Continued)

FOREIGN PATENT DOCUMENTS

EP 0223374 5/1987

(Continued)

*Primary Examiner*—Mary Lynn Theisen

(57) ABSTRACT

A vascular prosthesis comprising a first layer having a predetermined first porosity and a second layer having a predetermined second porosity, wherein the first layer and the second layer are each made of first and second electrospun polymer fibers.

35 Claims, 11 Drawing Sheets

U.S. PATENT DOCUMENTS

| | | | |
|---|---|---|---|
| 4,769,030 | A | 9/1988 | Pinchuk |
| 4,798,606 | A | 1/1989 | Pinchuk |
| 4,842,505 | A | 6/1989 | Annis et al. |
| 4,872,455 | A | 10/1989 | Pinchuk et al. |
| 4,880,002 | A | 11/1989 | MacGregor |
| 4,904,174 | A | 2/1990 | Moosmayer et al. |
| 4,905,367 | A | 3/1990 | Pinchuk et al. |
| 4,965,110 | A | 10/1990 | Berry |
| 4,990,158 | A | 2/1991 | Kaplan et al. |
| 4,997,600 | A | 3/1991 | Okumura et al. |
| 5,019,090 | A | 5/1991 | Pinchuk |
| 5,024,671 | A | 6/1991 | Tu et al. |
| 5,024,789 | A * | 6/1991 | Berry ........................... 264/6 |
| 5,084,065 | A | 1/1992 | Weldon et al. |
| 5,092,877 | A | 3/1992 | Pinchuk |
| 5,116,360 | A | 5/1992 | Pinchuk et al. |
| 5,133,742 | A | 7/1992 | Pinchuk |
| 5,147,725 | A | 9/1992 | Pinchuk |
| 5,226,913 | A | 7/1993 | Pinchuk |
| 5,298,255 | A | 3/1994 | Sawamoto et al. |
| 5,334,201 | A | 8/1994 | Cowan |
| 5,360,397 | A | 11/1994 | Pinchuk |
| 5,376,117 | A | 12/1994 | Pinchuk et al. |
| 5,383,922 | A | 1/1995 | Zipes et al. |
| 5,383,928 | A | 1/1995 | Scott et al. |
| 5,415,664 | A | 5/1995 | Pinchuk |
| 5,419,760 | A | 5/1995 | Narciso, Jr. |
| 5,545,208 | A | 8/1996 | Wolff et al. |
| 5,549,663 | A | 8/1996 | Cottone, Jr. |
| 5,554,722 | A | 9/1996 | Eichenauer et al. |
| 5,558,809 | A | 9/1996 | Groh et al. |
| 5,575,818 | A | 11/1996 | Pinchuk |
| 5,591,227 | A | 1/1997 | Dinh et al. |
| 5,609,629 | A | 3/1997 | Fearnot et al. |
| 5,624,411 | A | 4/1997 | Tuch |
| 5,628,788 | A | 5/1997 | Pinchuk |
| 5,632,772 | A | 5/1997 | Alcime et al. |
| 5,637,113 | A | 6/1997 | Tartaglia et al. |
| 5,639,278 | A | 6/1997 | Dereume et al. |
| 5,653,747 | A | 8/1997 | Dereume |
| 5,697,967 | A | 12/1997 | Dinh et al. |
| 5,700,269 | A | 12/1997 | Pinchuk et al. |
| 5,723,004 | A | 3/1998 | Dereume et al. |
| 5,725,567 | A | 3/1998 | Wolff et al. |
| 5,726,107 | A | 3/1998 | Dahringer et al. |
| 5,733,327 | A | 3/1998 | Igaki et al. |
| 5,741,333 | A | 4/1998 | Frid |
| 5,749,921 | A | 5/1998 | Lenker et al. |
| 5,755,722 | A | 5/1998 | Barry et al. |
| 5,755,774 | A | 5/1998 | Pinchuk |
| 5,766,710 | A | 6/1998 | Turnlund et al. |
| 5,797,887 | A | 8/1998 | Rosen et al. |
| 5,824,048 | A | 10/1998 | Tuch |
| 5,824,049 | A | 10/1998 | Ragheb et al. |
| 5,837,008 | A | 11/1998 | Berg et al. |
| 5,843,172 | A | 12/1998 | Yan |
| 5,849,037 | A | 12/1998 | Frid |
| 5,855,598 | A | 1/1999 | Pinchuk |
| 5,871,538 | A | 2/1999 | Dereume |
| 5,900,246 | A | 5/1999 | Lambert |
| 5,928,247 | A | 7/1999 | Barry et al. |
| 5,938,697 | A | 8/1999 | Killion et al. |
| 5,948,018 | A * | 9/1999 | Dereume et al. .......... 623/1.12 |
| 5,968,070 | A | 10/1999 | Bley et al. |
| 5,968,091 | A | 10/1999 | Pinchuk et al. |
| 5,980,551 | A | 11/1999 | Summers et al. |
| 5,980,972 | A | 11/1999 | Ding |
| 6,001,125 | A | 12/1999 | Golds et al. |
| 6,004,346 | A | 12/1999 | Wolff et al. |
| 6,013,099 | A | 1/2000 | Dinh et al. |
| 6,017,362 | A | 1/2000 | Lau |
| 6,019,789 | A | 2/2000 | Dinh et al. |
| 6,102,939 | A | 8/2000 | Pinchuk |
| 6,106,913 | A | 8/2000 | Scardino et al. |
| 6,117,425 | A | 9/2000 | MacPhee et al. |
| 6,165,212 | A | 12/2000 | Dereume et al. |
| 6,252,129 | B1 | 6/2001 | Coffee |
| 6,265,333 | B1 | 7/2001 | Dzenis et al. |
| 6,270,793 | B1 | 8/2001 | Van Dyke et al. |
| 6,306,424 | B1 | 10/2001 | Vyakarnam et al. |
| 6,308,509 | B1 | 10/2001 | Scardino et al. |
| 6,309,413 | B1 | 10/2001 | Dereume et al. |
| 6,604,925 | B1 | 8/2003 | Dubson |
| 2001/0020652 | A1 | 9/2001 | Kadlubowski |
| 2002/0002395 | A1 | 1/2002 | Berg et al. |

FOREIGN PATENT DOCUMENTS

| | | |
|---|---|---|
| EP | 0253539 | 1/1988 |
| EP | 0523960 | 1/1993 |
| GB | 2142870 | 1/1985 |
| WO | WO 01/54667 | 5/2002 |
| WO | WO 02/40242 | 5/2002 |

* cited by examiner

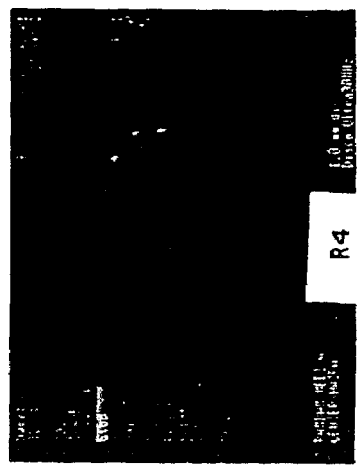
Fig. 13a(iii)
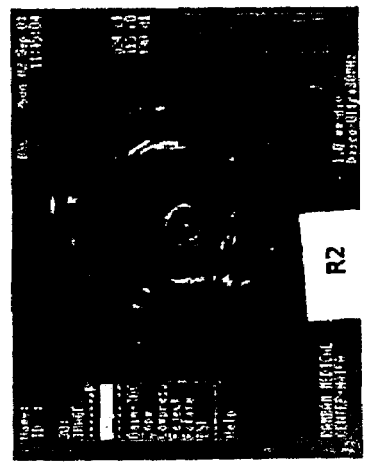
Fig. 13a(iv)
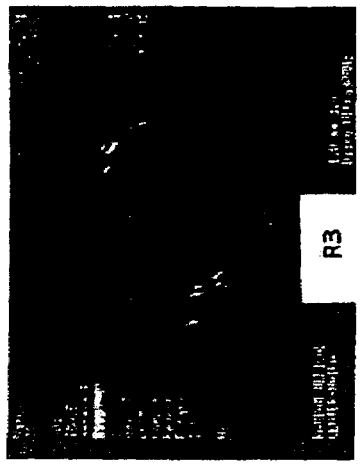
Fig. 13a(i)
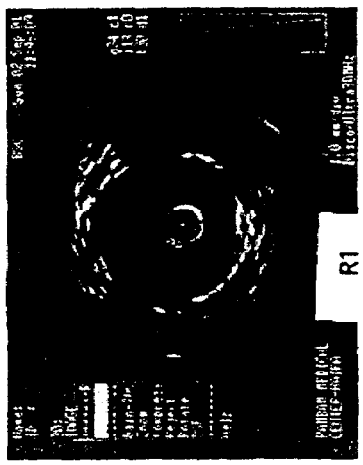
Fig. 13a(ii)

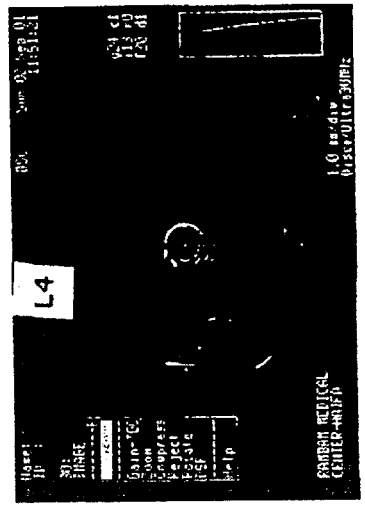
Fig. 13b(iii)
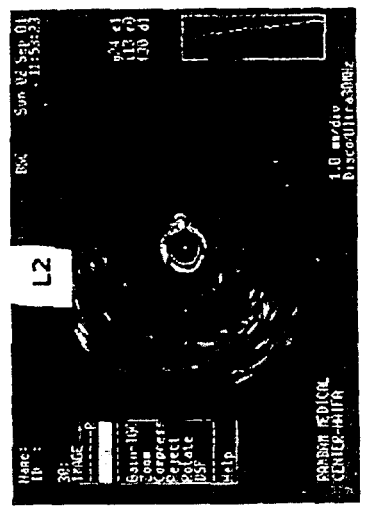
Fig. 13b(iv)
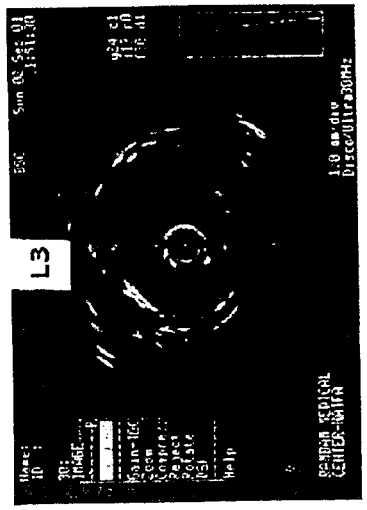
Fig. 13b(i)
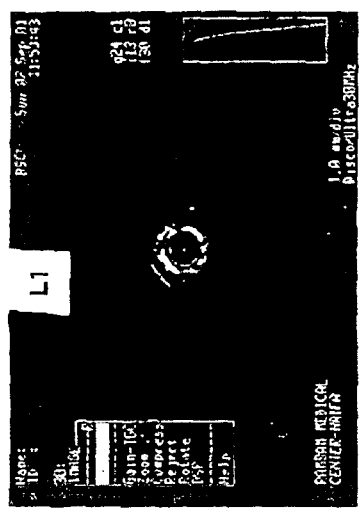
Fig. 13b(ii)

VASCULAR PROSTHESIS AND METHOD FOR PRODUCTION THEREOF

RELATED PATENT APPLICATION

This application is a National Phase Application of PCT/IL01/01172 International Filing Date 17 Dec. 2001, which claims priority from U.S. patent application Ser. No. 09/982,017 filed 19 Oct. 2001, which claims priority from U.S. Provisional Patent Application Nos. 60/276,956 filed 20 Mar. 2001 and 60/256,323 filed 19 Dec. 2000.

FIELD AND BACKGROUND OF THE INVENTION

The present invention relates to an improved vascular prosthesis and, more particularly, to a non-woven vascular prosthesis having improved biological, physical and mechanical properties and improved drug-delivery capability.

Tubular prostheses are commonly used as vascular grafts to replace or bypass damaged or diseased veins and arteries. When replacing blood vessels, grafts should have radial tensile strength sufficient to resist tearing and collapse in response to the pulsating pressure of the blood flowing therethrough. The elastic properties of grafts are crucial in order to allow conformation to the complex geometry of the body. Therewithal, grafts should be able to bend without breaking and without kinking, in order to ensure continues blood flow.

Artificial blood vessels and vascular prostheses are well known in the art. In particular, prosthetic devices made of polymer materials which typically exhibit a microporous structure that in general allows healthy tissue growth and cell endothelization, thus contributing to the long term healing and patency of the prostheses. Grafts having sufficient porous structure tend to promote tissue ingrowth and cell endothelization along the inner surface thereof. Increasing the porosity of vascular grafts leads to high permeability to blood during and following implantation. A typical method for avoiding severe blood leakage during implantation, is to clot the graft before implantation by patient blood or a biodegradable component such as albumin, gelatin, collagen or fibrin. Another disadvantage of highly porous vascular grafts, is a considerable reduction of the mechanical and tensile strength of the graft, and as a consequence the ability of the graft to remain in the proper position inside the body vasculature becomes weak. Furthermore, low mechanical and tensile strength may even lead to tearing of the graft. Examples for highly porous grafts are polyethylene terephtalat (PET) vascular prostheses fabricated as woven or knitted textiles which are disclosed in, for example, U.S. Pat. Nos. 5,527,353; 4,441,215; 4,695,280; and 5,584,875.

In a natural arterial tissue, the diameter of the blood vessel may vary up to 15% as a function of blood pressure. This characteristic of natural blood vessels, named compliance, is of crucial importance when manufacturing an artificial blood vessel. A compliant wall should act as an elastic reservoir, absorbing energy during systole and releasing energy during diastole. A rigid vessel wall diminishes the pulsatile component of the diastolic recoil, thereby reducing the energy available for distal perfusion. It has been demonstrated experimentally that incompatible compliance of a vascular graft and the host artery is detrimental to graft performance [Baird R. N., Abbott W. M. "Pulsatile blood-flow in arterial grafts", The Lancet 1976; 30; 948–9; Abbott W. M., Megerman J. M. et al. "Effect of compliance mismatch upon vascular graft patency", J. Vasc. Surg. 1987, 5; 376–82].

Over the years, efforts have been made to fabricate prosthetic grafts having compliance, which are similar to that found in human arteries [Reed A. M., Potter J, Szycher M., "A solution grade biostable polyurethane elastomer: Chronoflex AR" Journal of Biomaterials Applications 1994; 8:210–36; Edwards A, Carson R. J, Bowald S., "Development of microporous small bore vascular graft", Journal of Biomaterials Applications 1995; 10:171–87]. Hence, many vascular grafts are either available commercially, or presently under development [Brewster D. C., Rutherford R. B., "Prosthetic Grafts", Vascular Surgery 4th ed. Philadelphia; Saunders W. B., 1995; 492–521; Quinones-Baldrich W. J., Busutill R. W., Baker I. D. et al. "Is the preferential use of PTFE grafts for femoropopliteal bypass justified?", J. Vasc. Surg. 1988; 219–228]. However, no known graft material has satisfactory compliance properties.

Large and moderate diameter, vascular prostheses are typically made of expanded polytetrafluorethylene (ePTFE), by extrusion, drawing and sintering process to produce a tube with a porous wall. Grafts made of ePTFE and methods for the production thereof are found, for example, in U.S. Pat. Nos. 5,628,786; 4,306,318; and 5,061,276. In regard to improved mechanical strength of vascular grafts, different ePTFE grafts have been proposed, and can be found for example in U.S. Pat. No. 6,001,125, which relates to an implantable microporous ePTFE vascular prosthesis having multiple layers. An additional example is U.S. Pat. No. 5,628,786 which discloses a vascular graft formed of ePTFE having a reinforced structure that enables radial expansion of the graft and that stabilizes the graft against longitudinal compression. However, ePTFE suffer inherently from low compliance, which limit the use thereof when manufacturing vascular grafts.

Attempts have also been made to provide grafts characterized by both high compliance and high porosity, by the utilization of fiber polyurethanes. However, many polyurethanes, including those based on polycarbonate soft segments, have insufficient long-term biostability. Recently, siloxane-based aromatic polyurethanes have been developed, which have acceptable biostability even for thin fibers [In Vivo Degradation of Polyurethanes: Transmission FTIR Microscopic Characterization of Polyurethanes Sectioned by Cryomicroscopy. MaCarthy S. J. at al., Biomaterials, 18, 1387 (1997); Polydimethylsiloxane (polyether-mixed macrodiol-based polymethane elastomers) biostability, Martin D. J. et al., Biomaterials, 21, 1021–1029 (2000); PCTAU 91/00270; PCT/AU 99/00236; PCTAU 98/00497; PP 9917].

Electrospinning is a method for the manufacture of ultrathin synthetic fibers which reduces the number of technological operations and increases the stability of properties of the product being manufactured. In regard to vascular prostheses, electrospinning and electrospinning-like manufacturing methods are disclosed, for example, in U.S. Pat. Nos. 4,562,707, 4,645,414, 5,639,278, 5,723,004 and 5,948,018. According to the electrospinning method, fibers of a given length are formed during the process of polymer solution flow from capillary apertures under electric forces and fall on a receptor to form a non-woven polymer material, the basic properties of which may be effectively altered. Being electrically charged, the fibers fall on the receptor in a manner that minimizes the pore size deviation. As stated, high porosity may affect the mechanical and tensile strength of the graft.

There is thus a widely recognized need for, and it would be highly advantageous to have, a vascular prosthesis and method for production thereof, devoid of the above limitations.

SUMMARY OF THE INVENTION

According to one aspect of the present invention there is provided a vascular prosthesis comprising a first layer having a predetermined first porosity and a second layer having a predetermined second porosity, wherein the first layer and the second layer are each made of first and second electrospun polymer fibers.

According to another aspect of the present invention there is provided a vascular prosthesis made of at least one biocompatible material, the vascular prosthesis having at least two characteristics selected from the group consisting of: (a) having an inner diameter expandable by at least 5% under a pulsatile pressure characterizing a mammalian blood system; (b) capable of maintaining the inner diameter while bent at a bent diameter of twice the inner diameter; (c) having a porosity of at least 60%; (d) preventing leakage of blood passing therethrough; (e) characterized by tissue ingrowth and cell endothelization over at least 90% of the vascular prosthesis within at least 10 days from implantation in a mammal; and (f) having a self-sealing properties so as to minimize blood leakage following piercing.

According to yet another aspect of the present invention there is provided a method of replacing a portion of a blood vessel, comprising: providing a vascular prosthesis as described herein; excising the portion of the blood vessel, thereby creating a pair of blood vessel ends; and connecting the vascular prosthesis to the pair of blood vessel ends so as to allow blood flow through the vascular prosthesis.

According to still another aspect of the present invention there is provided a method of bypassing an obstructed portion of a blood vessel, comprising: providing a vascular prosthesis as described herein; forming a pair of holes in the blood vessel upstream and downstream the obstruction; and connecting the vascular prosthesis to the pair of holes so as to allow blood flow through the vascular prosthesis.

According to an additional aspect of the present invention there is provided a method of connecting a pair of blood vessels, comprising: providing a vascular prosthesis as described herein; forming a pair of holes in the pair of blood vessels; and connecting the vascular prosthesis to the pair of holes so as to allow blood flow through the vascular prosthesis, thereby connecting the pair of blood vessels.

According to further features in preferred embodiments of the invention described below, the blood vessel is selected from the group consisting of a peripheral blood vessel, a vein and a coronary artery.

According to yet an additional aspect of the present invention there is provided a method of producing a vascular prosthesis, the method comprising: electrospinning a first liquefied polymer onto a precipitation electrode hence providing a first layer having a predetermined first porosity; and electrospinning a second liquefied polymer onto the precipitation electrode hence providing a second layer having a predetermined second porosity.

According to further features in preferred embodiments of the invention described below, the precipitation electrode is a rotating mandrel.

According to still further features in the described preferred embodiments the method further comprising electrospinning at least one additional liquefied polymer onto the precipitation electrode prior to the step of electrospinning the second liquefied polymer, hence providing at least one intermediate layer interposed between the first layer and the second layer.

According to still further features in the described preferred embodiments each of the electrospinning steps comprising: (a) charging the liquefied polymer, thereby producing a charged liquefied polymer; (b) subjecting the charged liquefied polymer to a first electric field; and (c) dispensing the charged liquefied polymers within the first electric field in a direction of the precipitation electrode.

According to still further features in the described preferred embodiments the first electric field is defined between the precipitation electrode and a dispensing electrode being at a first potential relative to the precipitation electrode.

According to still further features in the described preferred embodiments the method further comprising providing a second electric field defined by a subsidiary electrode being at a second potential relative to the precipitation electrode, the second electric field being for modifying the first electric field.

According to still further features in the described preferred embodiments the subsidiary electrode serves for reducing non-uniformities in the first electric field.

According to still further features in the described preferred embodiments the subsidiary electrode serves for controlling fiber orientation of the polymer fiber shell generated upon the precipitation electrode.

According to still further features in the described preferred embodiments the method further comprising winding a filament around at least one of the first layer and the second layer, hence providing at least one layer which comprises at least one coiled pattern.

According to still further features in the described preferred embodiments the filament is formed by polymer fiber extruder.

According to still further features in the described preferred embodiments the polymer filament extruder includes a bath for holding a melted polymer.

According to still further features in the described preferred embodiments the melted polymer is a biocompatible melted polymer.

According to still further features in the described preferred embodiments at least a portion of the biocompatible melted polymer includes a melted polyurethane.

According to still further features in the described preferred embodiments the method further comprising cooling the filament by airflow upon exiting the polymer fiber extruder.

According to still further features in the described preferred embodiments the step of winding and at least one of the steps of electrospinning are performed simultaneously.

According to still further features in the described preferred embodiments the method further comprising coating the filament by a polyurethane solution prior to the step of winding the filament.

According to still further features in the described preferred embodiments the coating comprises dipping the filament into the polyurethane solution.

According to still further features in the described preferred embodiments the method further comprising heating the filament prior to, during or subsequent to the step of winding the filament.

According to still further features in the described preferred embodiments the method further comprising heating the mandrel prior to, during or subsequent to the step of electrospinning.

According to still further features in the described preferred embodiments heating the mandrel is selected from the group consisting of external heating and internal heating.

According to still further features in the described preferred embodiments the external heating is by at least one infrared radiator.

According to still further features in the described preferred embodiments the at least one infrared radiator is an infrared lamp.

According to still further features in the described preferred embodiments the internal heating is by a built-in heater.

According to still further features in the described preferred embodiments the built-in heater is an Ohmic built-in heater.

According to still further features in the described preferred embodiments the method further comprising winding a filament around at least one of the at least one intermediate layer, hence providing at least one layer which comprises at least one coiled pattern.

According to still further features in the described preferred embodiments each of the first liquefied polymer, the second liquefied polymer and the at least one additional liquefied polymer are independently biocompatible.

According to still further features in the described preferred embodiments each of the first liquefied polymer, the second liquefied polymer and the at least one additional liquefied polymer is independently selected from the group consisting of polyethylene terephtalat fibers, and polyurethane fibers.

According to still further features in the described preferred embodiments the method further comprising incorporating at least one drug within at least one of the first liquefied polymer, the second liquefied polymer and the at least one additional liquefied polymer, for delivery of the at least one drug into a body vasculature during or after implantation of the vascular prosthesis within the body vasculature.

According to still further features in the described preferred embodiments each of the first liquefied polymer, the second liquefied polymer and the at least one additional liquefied polymer are independently combination of a biodegradable liquefied polymer and a biostable liquefied polymer.

According to still further features in the described preferred embodiments the first and second electrospun polymer fibers are made from the same polymer.

According to still further features in the described preferred embodiments the first and second electrospun polymer fibers are made from different polymers.

According to still further features in the described preferred embodiments the first layer is an inner layer and the second layer is an outer layer.

According to still further features in the described preferred embodiments each of the first layer and the second layer is independently of a tubular structure.

According to still further features in the described preferred embodiments the vascular prosthesis further comprising at least one intermediate layer interposed between the first layer and the second layer.

According to still further features in the described preferred embodiments the at least one intermediate layer comprises at least one coiled pattern.

According to still further features in the described preferred embodiments the coiled pattern is formed from a wound filament.

According to still further features in the described preferred embodiments the coiled pattern is embodied within the first layer.

According to still further features in the described preferred embodiments the coiled pattern is embodied within the second layer.

According to still further features is the described perferred embodiments the wound filament is selected from the group consisting of a wound polypropylene filament and a wound polyurethane filament.

According to still further features in the described preferred embodiments the wound filament is coated by a polyurethane solution.

According to still further features in the described preferred embodiments the wound filament has a cross-section selected from the group consisting of a circular cross section, an ellipsoid cross section a polygonal cross section and an irregular pattern cross section.

According to still further features in the described preferred embodiments the at least one intermediate layer includes a plurality of adhesion sublayers, alternately interposed between the first layer and the coiled pattern, between the coiled pattern and the second layer, and between two congruent coiled patterns.

According to still further features in the described preferred embodiments the adhesion sublayers are impervious adhesion sublayers.

According to still further features in the described preferred embodiments the adhesion sublayers are formed from electrospun polymer fibers.

According to still further features in the described preferred embodiments the at least one intermediate layer has a predetermined porosity.

According to still further features in the described preferred embodiments the at least one intermediate layer is made of third electrospun polymer fibers.

According to still further features in the described preferred embodiments the first and the second electrospun polymer fibers are biocompatible.

According to still further features in the described preferred embodiments the first, the second and the third electrospun polymer fibers are each independently biocompatible.

According to still further features in the described preferred embodiments each of the first, the second and the third electrospun polymer fibers are independently selected from the group consisting of polyethylene terephtalat fibers and polyurethane fibers.

According to still further features in the described preferred embodiments the first and the second electrospun polymer fibers are selected from the group consisting of polyethylene terephtalat fibers and polyurethane fibers.

According to still further features in the described preferred embodiments each of the first layer and the second layer independently includes at least one drug incorporated therein, for delivery of the at least one drug into a body vasculature during or after implantation of the vascular prosthesis within the body vasculature.

According to still further features in the described preferred embodiments the first polymer fibers are made from a combination of a biodegradable polymer and a biostable polymer.

According to still further features in the described preferred embodiments the at least one intermediate layer includes at least one drug incorporated therein for delivery of the at least one drug into a body vasculature during or after implantation of the vascular prosthesis within the body vasculature.

According to still further features in the described preferred embodiments the second polymer fibers are made from a combination of a biodegradable polymer and a biostable polymer.

The present invention successfully addresses the shortcomings of the presently known configurations by providing a vascular prosthesis and a method for manufacturing thereof, the vascular prosthesis enjoys both mechanical and biological properties far exceeding the prior art.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 13a(i)–(iv) show results of inter vascular ultrasound (IVUS) image investigation, according to the teachings of the present invention; and FIG. 13b(i)–(iv) show results of IVUS image investigation, according to prior art teachings.

DESCRIPTION OF THE PREFERRED EMBODIMENTS

Figure 1A:
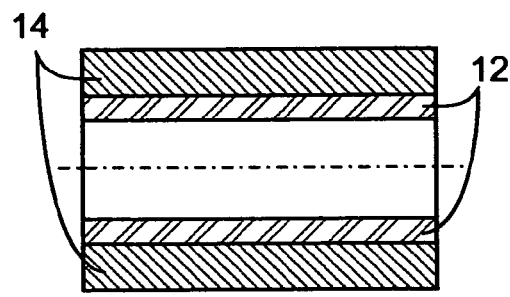
FIG. 1a is a longitudinal cross-sectional view of a vascular prosthesis having a first layer and a second layer according to the present invention.
Figure 1B:
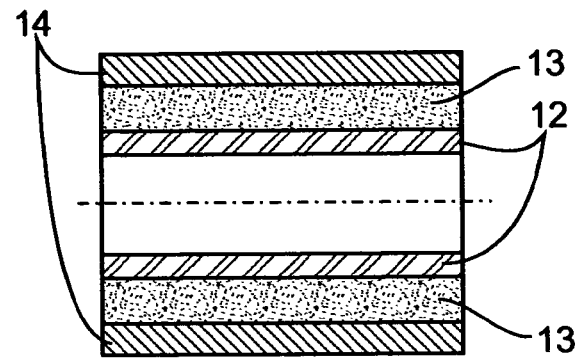
FIG. 1b is a longitudinal cross-sectional view of the vascular prosthesis further including an intermediate layer, according to the present invention.

The present invention is of a vascular prosthesis having improved biological, physical and mechanical properties, which can be implanted in a mammal. Specifically, the present invention can be used to replace, bypass or connect blood vessels and other fluid-transporting vessels of the body, for example, coronary arteries, peripheral blood vessels, urinary vessels and the like.

The principles and operation of a vascular prosthesis according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to the drawings, FIGS. 1a–d illustrates a longitudinal cross-sectional view of a vascular prosthesis constructed and manufactured in accordance with the teachings of the present invention. As shown in FIG. 1a, the vascular prosthesis includes a first layer 12 having a predetermined first porosity and a second layer 14 having a predetermined second porosity, wherein first layer 12 and second layer 14 are each made of first and second electrospun polymer fibers, respectively. According to a preferred embodiment of the present invention, first layer 12 is an inner layer and second layer 14 is an outer layer.

First layer 12 is preferably manufactured substantially as a smooth surface with relatively low porosity. First layer 12 serves as a sealing layer to prevent bleeding, hence precludes preclotting, the rate of which is known to be high up to several hours after implantation. In addition, throughout the life of the vascular prosthesis, first layer 12 ensures antithrombogenic properties and efficient endothelization of the inner surface of the vascular prosthesis. A typical thickness of first layer 12 is ranging from about 40 µm to about 80 µm.

Figure 2:
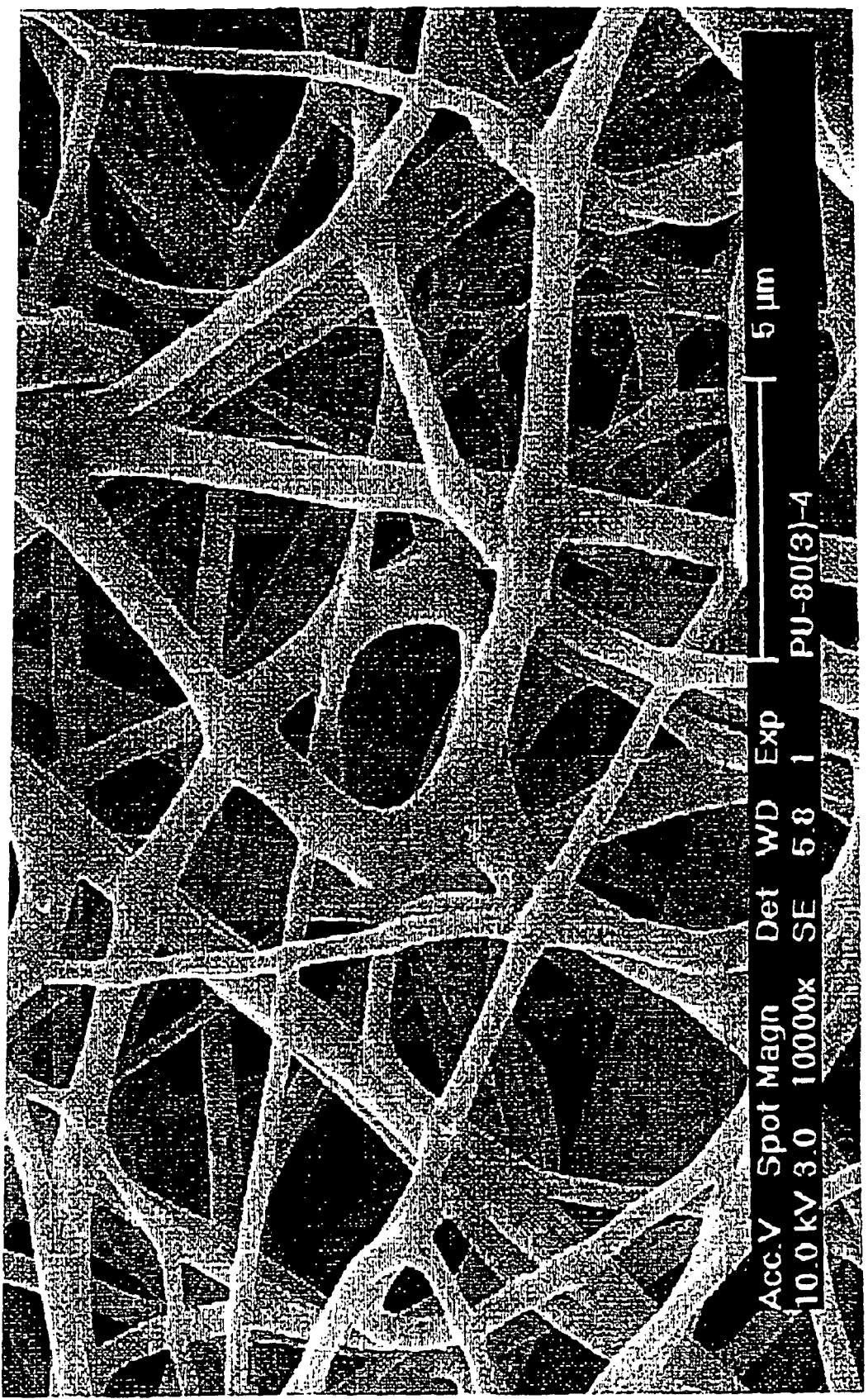
FIG. 2 is a typical structure of a porous layer, according to the teachings of the present invention.

According to a preferred embodiment of the present invention second layer 14 provides requisite mechanical properties of the vascular prosthesis, specifically high compliance and high breaking strength, hence the thickness of second layer is preferably larger than the thickness of first layer 12. A typical thickness of second layer 14 is ranging from about 50 µm to about 1000 µm. In addition, the predetermined porosity of second layer 14 is preferably larger than the predetermined porosity of first layer 12. A porous structure is known to promote ingrowth of surrounding tissues, which is extremely important for fast integration and long-term patency of the vascular prosthesis. An example of the porous structure of second layer 14 is shown in FIG. 2.

A method of achieving a combination of high compliance and high breaking strength is further detailed hereinafter.

According to a presently preferred embodiment of the present invention, the vascular prosthesis further includes at least one intermediate layer 13 (shown in FIG. 1b), interposed between first layer 12 and second layer 14, each of layers 13 is made of third electrospun polymer fibers and having a predetermined porosity. In the presently preferred embodiment of the invention, porosity level is a decreasing function of a distance of the layer from the center of the vascular prosthesis, however it should be appreciated that in other embodiments any predetermined porosity distributions may be employed. A multilayer vascular prosthesis can be used in cases of high bleeding hazard, for example, upon implantation of a shunt, which serves as a channel for fluid delivery in or out of the body vasculature.

Drug delivery into a body vasculature can be performed during or after implantation of the vascular prosthesis within the body vasculature. Hence, according to a preferred embodiment of the present invention, each of first layer 12 second layer 14 or any intermediate layer(s) 13 may incorporate at least one drug therein, for delivery into body vasculature by, for example, a slow release mechanism. It is appreciated that the drug incorporated, as well as the concentration and method of incorporation into the prosthesis is in accordance with the type of vessel being replaced, and with the particular pathology of the patient.

Figure 1C:
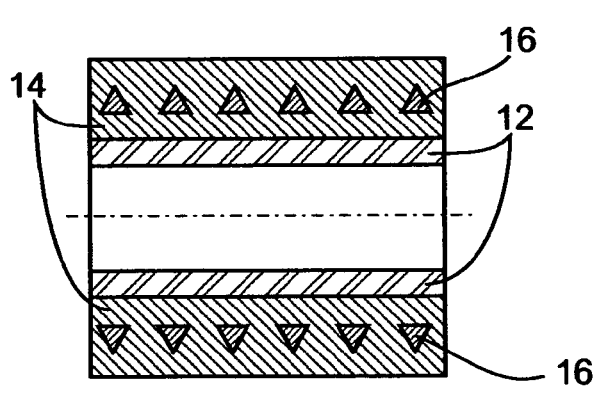
FIG. 1c is a longitudinal cross-sectional view of the vascular prosthesis further including a coiled pattern according to the present invention.
Figure 8:
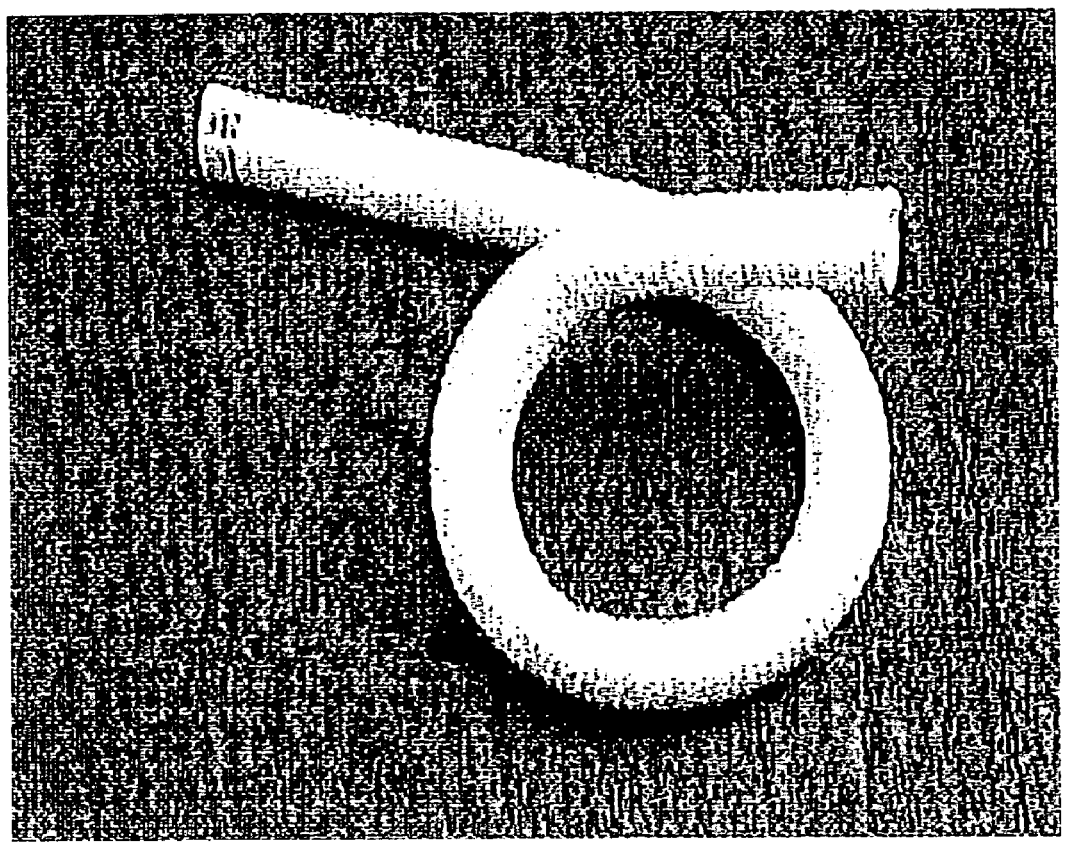
FIG. 8 is a reinforced vascular graft.

Reference is now made to FIG. 1c, which depicts a longitudinal cross-sectional view of the vascular prosthesis, demonstrating another preferred embodiment of the invention. Hence, the vascular prosthesis may further include at least one coiled pattern 16, which serve for reinforcing of the vascular prosthesis specifically for enhancing anti-kinking properties. Reinforced vascular prosthesis can be used, for example, upon implantation of long grafts within body vasculature, where the graft should fit the complex geometry of the host. An example of a reinforced graft is shown in FIG. 8 (further described in the Examples section below).

In accordance with the presently preferred embodiment of the invention, coiled pattern 16 is formed from a wound filament, which may be for example, a wound polypropylene filament or a wound polyurethane filament. The transverse cross section of the wound filament may be chosen so as to increase the mechanical properties of the vascular prosthesis.

Figure 7:
FIG. 7 shows cross-sectional shapes, which may be used for providing a coiled pattern according to the present invention.
Figure 7:
Figure 7:

As shown in FIG. 1c, the wound filament has a triangular cross section, however any other transverse cross sections may be selected, for example a polygonal (other than a triangle) cross sections, a circular cross section, an ellipsoid cross section and an irregular pattern cross section. Preferred cross sections in accordance with the presently preferred embodiment of the invention, are shown in FIG. 7, further detailed hereinafter.

Figure 1D:
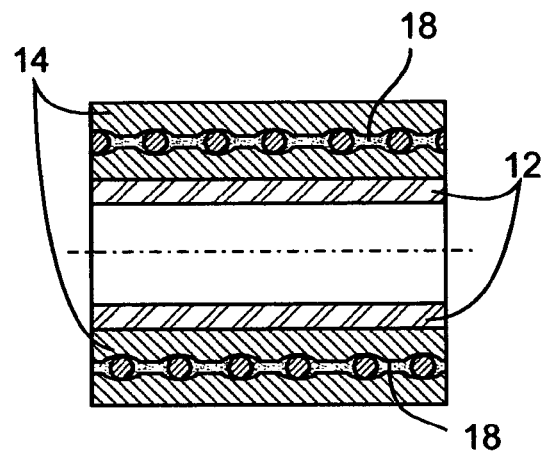
FIG. 1d is a longitudinal cross-sectional view of the vascular prosthesis further including a plurality of adhesion sublayers according to the present invention.

Referring now to FIG. 1d, which is still a longitudinal cross-sectional view of the vascular prosthesis. The vascular prosthesis may further include a plurality of adhesion sublayers 18, alternately interposed between first layer 12 and coiled pattern 16, between coiled pattern 16 and second layer 14, and between two congruent coiled patterns (in cases where more than a single coiled pattern exists). Adhesion sublayers 18 serve for adhering the various layers to one another and may be either impervious or permeable. FIG. 1d shows adhesion sublayers 18, which adhere coiled pattern 16 (shown in FIG. 1d with a circular cross section) to second layer 14 on one side and to an intermediate layer 20 made of electrospun polymer fibers on the other side.

It should be understood that in some preferred embodiments of the present invention adhesion sublayers 18, are not needed as the production process further detailed hereinunder ensures stability of the vascular prosthesis.

The present invention successfully addresses the problem of existing vascular access graft (VAG), also known as an AV-shunt. In addition to the above requirements of conventional peripheral grafts VAG should possess specific constructive features. Being internally accessed a plurality of times, VAG should in principle combine preservation of the mechanical properties, as well as self-sealing properties, so as to minimize blood leakage following piercing and prevent hematomas, which normally follows each piercing, such as a dialysis needle piercing. Moreover, VAG should be suitable for fast implantation and puncturing without any special preparatory operations.

Piercing of existing VAGs oftentimes results in significant bleeding, depending on the material's elasticity. For all of the presently known VAGs, each piercing is followed by a substantial signature of a "non-healing" puncture, which over time and repetitive piercing, hampers the VAG mechanical properties. The signature stems from the fact that a dialysis needle, which is typically of a relatively large diameter (up to 2 mm), penetrates through the VAG wall and irreversibly ruptures it.

Hence, according to a preferred embodiment of the present invention, there is provided a triple-layered VAG, having an inner layer, an intermediate layer and an outer layer. The inner layer and the outer layer each formed from crude fibers with predominantly transverse (polar) orientation, with a predetermined porosity ranging from about 50% to about 70%. Whereas an intermediate layer is formed from thin and randomly-oriented fibers, with a predetermined porosity ranging from about 80% to about 90%. Preferably, the intermediate layer comprises about 70% of the overall VAG wall thickness. In accordance to the presently preferred embodiment of the invention, the inner layer and the outer layer, serve for supporting the intermediate layer.

Upon puncturing, a needle passes through the intermediate layer, by forcing the fibers apart, hence no rupturing occurs. The tearing is prevented due to the combination of high elasticity of the fibers, large number of voids and small number of bonds between the fibers. Once the needle extracted out of the VAG the original fibers web is reconstructed, both because of the fiber elasticity and because the pressure applied by the inner and outer layers. Thus, high level of graft sealing or reannealing is achieved.

The VAG strength properties are mainly ensured by its inner and outer layers. The piercing damage in the outer and inner layers are spread apart of one another by a certain distance, thus minimizing the affect of puncture on the wall strength.

According to a preferred embodiment of the present invention, VAG kink and compression resistance as well as self-sealing properties can be increased considerably by including a layer, which comprises a coiled pattern embodied therein, e.g., within at least one of the inner layer and the outer layer. In the case of including two coiled pattern, the coils are preferably contrary oriented.

The layers of the vascular prosthesis may be made from any known biocompatible polymer, such as but not limited to, polyethylene terephtalat fibers or polyurethane fibers. In a preferred embodiment in which the vascular prosthesis incorporates at least one drug for delivery of the drug into a body vasculature during or after implantation, the polymer fibers that form the relevant layer are a combination of a biodegradable polymer and a biostable polymer.

Hence, according to the preferred embodiments of the present invention, there is provided a vascular prosthesis, having various of physical, mechanical and biological properties, which properties are any combination of the following characteristics: (a) having an inner diameter expandable by at least 10% under a pulsatile pressure characterizing a mammalian blood system; (b) capable of maintaining said inner diameter while bent at a bent diameter of twice said inner diameter; (c) having a porosity of at least 60%; (d) preventing leakage of blood passing therethrough; (e) characterized by tissue ingrowth and cell endothelization over at least 90% of the vascular prosthesis within at least 10 days from implantation in a mammal; and (f) having a self-sealing properties so as to minimize blood leakage following piercing.

The combination of the vascular prosthesis mechanical characteristics, specifically high breaking strength, an admissible compliance level and porosity, stems from the electrospinning method of manufacturing, which is further described hereinunder. Although electrospinning can be efficiently used for generating large diameter shells, the nature of the electrospinning process prevents efficient generation of products having small diameters, such as vascular grafts. In particular, electrospinning manufacturing of small diameter grafts result in predominant axial orientation of the fibers leading to a considerable predominance of an axial over radial strength.

While reducing the present invention to practice, it was uncovered that proper compliance and at the same time improved mechanical strength can be achieved when substantially thick and strong fibers are situated axially, and substantially thin and highly elastic fibers are situated in a transverse (polar) direction.

Thus, according to the present invention there is provided a method of producing a vascular prosthesis. The method comprises electrospinning a first liquefied polymer onto a precipitation electrode hence providing first layer 12 (shown in FIG. 1a) having a predetermined first porosity. The method further comprises electrospinning a second liquefied polymer onto the precipitation electrode hence providing second layer 14 (shown in FIG. 1a) having a predetermined second porosity. The precipitation electrode, which serves for generating the vascular prosthesis thereupon, can be, for example, a rotating mandrel of uniform or varying radius, depending on the size of the vascular prosthesis to be fabricated.

As stated, in preferred embodiments of the invention, the vascular prosthesis may further includes at least one intermediate layer 13 interposed between first layer 12 and second layer 14. In such a case, the method further comprises electrospinning at least one additional liquefied polymer onto the precipitation electrode prior to the step of electrospinning the second liquefied polymer, hence providing at least one intermediate layer 13 interposed between first layer 12 and second layer 14.

Figure 3:
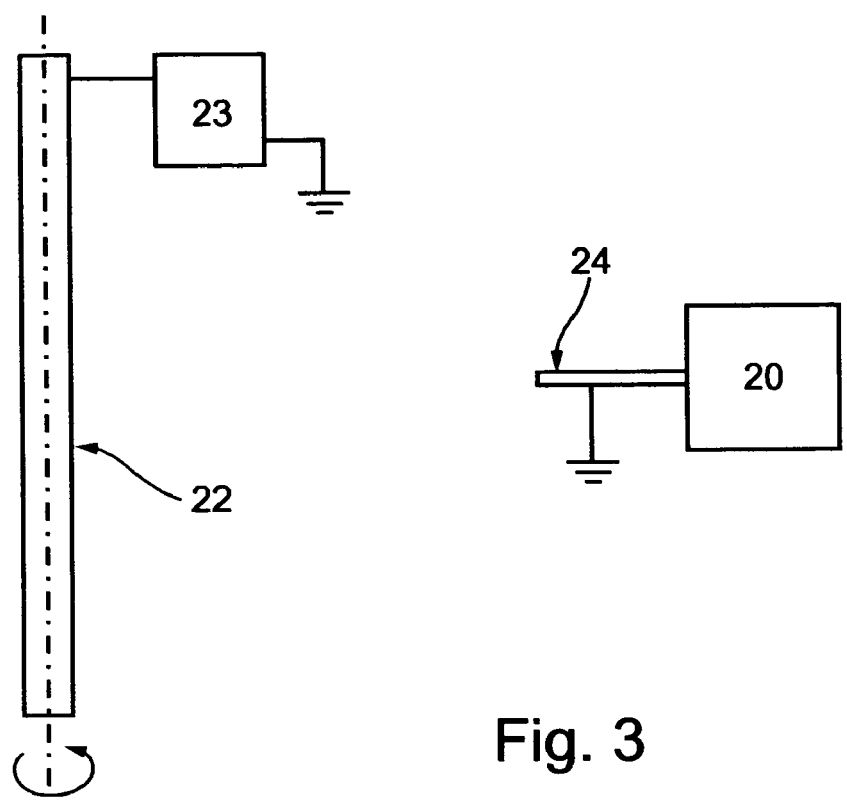
FIG. 3 is a typical, prior art, electrospinning apparatus.

The electrospinning steps may be performed using any electrospinning apparatus known in the art. Referring now again to the figures, FIG. 3 illustrate a typical electrospinning apparatus, which includes a pump 20, a precipitation electrode 22 connected to a power supply 23 and a dispensing electrode 24. Pump 20 serves for drawing the liquid polymer through a syringe (not shown in the figure) into dispensing electrode 24. Precipitation electrode 22 and dispensing electrode 24 are held under a first potential difference hence generating a first electric field therebetween. According to the electrospinning method, liquefied polymer is charged and drawn into dispensing electrode 24, and then, subjected to the first electric field, dispensed in a direction precipitation electrode 22. Moving with high velocity in the inter-electrode space, jets of liquefied polymer evaporate, thus forming fibers which are collected on the surface of precipitation electrode 22. A typical thickness of the fibers thus formed ranges between 50 nm and 50 μm.

Figure 4:
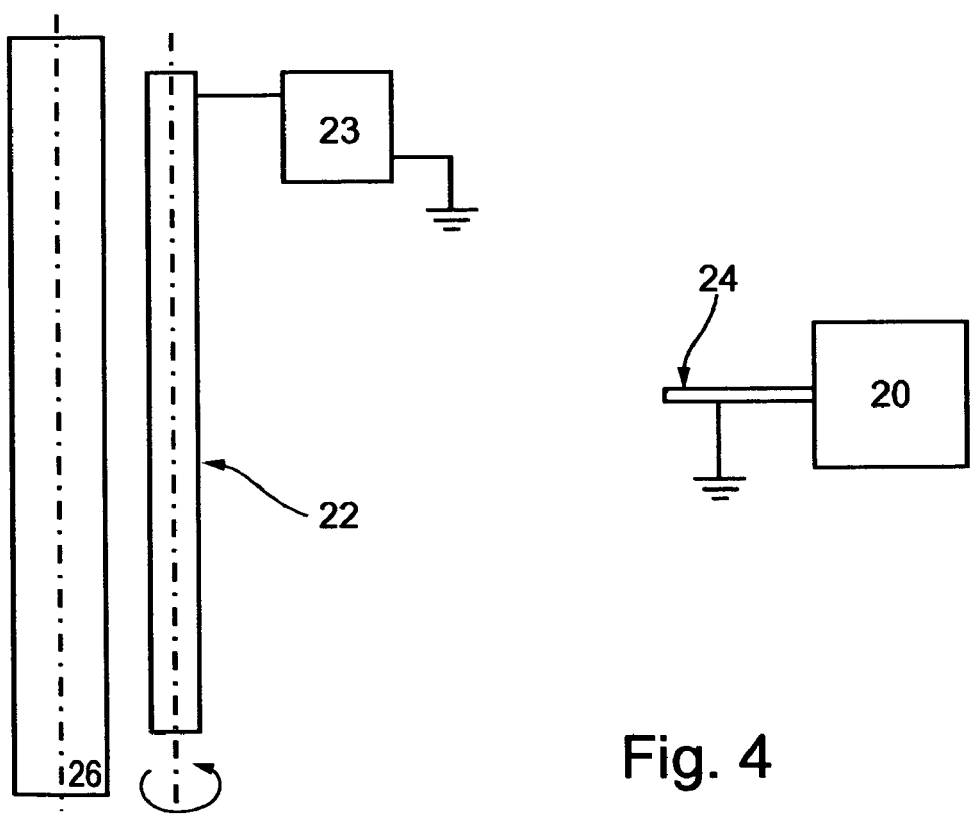
FIG. 4 is an electrospinning apparatus further including a subsidiary electrode according to the present invention.

Reference is now made to FIG. 4, which depicts electrospinning apparatus used according to another preferred embodiment of the present invention in the manufacturing of vascular prostheses. Hence, the method may further comprise providing a second electric field defined by a subsidiary electrode 26 which is kept at a second potential difference relative to precipitation electrode 22. The purpose of the second electric field (and of the subsidiary electrode 26) is to modify the first electric field so as to ensure a predetermined fiber orientation while forming the vascular prosthesis. As stated, such predetermined orientation is extremely important, in order to provide a vascular prosthesis combining the above structural characteristics.

The advantage of using the electrospinning method for fabricating vascular prosthesis is flexibility of choosing the polymer types and fibers thickness, thereby providing a final product having the required combination of strength, elastic and other properties as delineated herein. In addition, an alternating sequence of the layers, each made of differently oriented fibers, determines the porosity distribution nature along the vascular prosthesis wall thickness. Still in addition, the electrospinning method has the advantage of allowing the incorporation of various chemical components, such as drugs, to be incorporated in the fibers by dissolving such drugs in the liquefied polymers prior to electrospinning.

Thus, according to a preferred embodiment of the present invention, the method may further comprise incorporating at least one drug within at least one of the liquefied polymers, for the purpose of drug delivery into a body vasculature during or after implantation. Preferably, axial oriented fibers, which do not essentially contribute to the radial strength properties, can be made of biodegradable polymer and be drug-loaded. Such incorporation of drug results in slow release of the drug upon biodegradation of the fibers.

According to a preferred embodiment of the present invention, the method may further comprise winding filament 16 around at least one layer subsequent to its electrospinning formation, hence providing at least one layer, which comprises at least one coiled pattern. It should be appreciated that the step of winding and the electrospinning step may also be performed simultaneously. The winding step serves for reinforcement of the vascular prosthesis, as described hereinabove. The diameter of filament 16 can vary from about 0.2 mm to about 0.5 mm, depending on the diameter of the vascular prosthesis and the desired compliance. A typical winding pitch is from about 0.3 mm to about 1.5 mm. A typical tension employed on filament 16 upon winding is between about 0.1 N and about 0.5 N.

According to a preferred embodiment of the present invention, the method may further include a step of forming at least one adhesive sublayer, so as to adhere the components of the graft, specifically the coiled pattern to the electrospun layers. Adhesion may be employed in more than one way, as is further described herein.

Hence, according to a preferred embodiment of the invention, a first adhesion method comprises coating the layer onto which a coiled pattern is to be formed, with a layer of polymer fiber with a high degree of elasticity. The coating can be done by electrospinning a liquefied polymer, which is dissolved in a high boiling point solvent, thus forming a substantially impervious layer having adhesive properties.

Once an adhesive sublayer is formed, the winding step is employed and subsequently an additional adhesive sublayer is applied. Thus, according to the presently preferred embodiment of the invention, each coiled pattern is sandwiched between two adhesive sublayer. Such adhesion sublayers adheres tightly to the filament, and substantially decrease the permeability of the graft wall.

Figure 5:
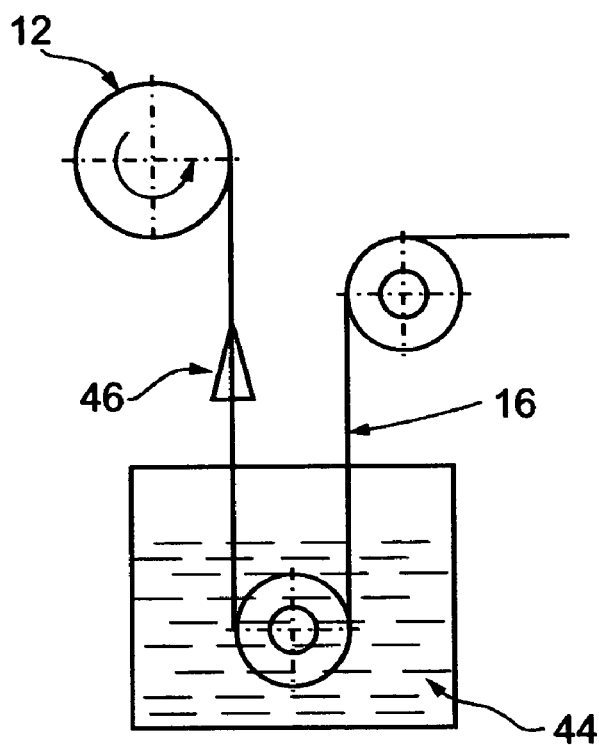
FIG. 5 is an apparatus for dipping a filament used during the step of winding according to the present invention.

A second adhesion method is illustrated in FIG. 5. A filament 16 which is used to form the coiled pattern, is immersed in a polyurethane solution 44 prior to the winding step, so as to provide a binding coat to the filament. The filament passes through a scraper 46 for removing excess of the binding coat therefrom, and winds preferably around first layer 12 of the vascular prosthesis. The binding coat ensures that the filament binds to the layer.

Figure 6:
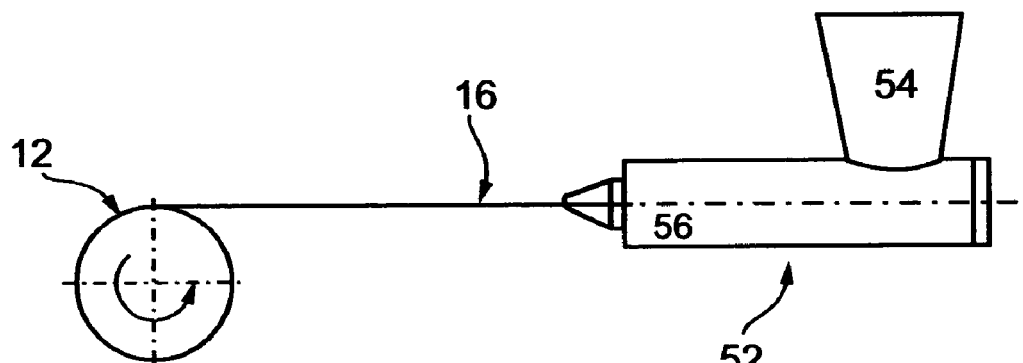
FIG. 6 is a polymer filament extruder used for generating the filament for the step of winding according to the present invention.

A third adhesion method is illustrated in FIG. 6. Filament 16 is generated by a polymer filament extruder 52 which includes a bath 54 holding a melted polymer, and a capillary 56 for extruding the generated filament in a direction of precipitation electrode 22. The advantage of this technique is that a broad scope of biocompatible polymers can be used, including various polyurethane compositions. An additional advantage of using polymer filament extruder 52 is illustrated in FIG. 7, showing cross-sectional shapes which may be used for filament 16. Polymer filament extruder 52 may provide any desired cross-sectional shape for filament 16, preferably of trapezoidal or triangular cross-section, for optimizing load distribution. It should be appreciated that any other cross-section may be used for filament 16, such as but not limited to, a circular cross section, an ellipsoid cross section or other irregular pattern cross sections A fourth adhesion method comprises heating the filament to a temperature ranging from about 120° C. to about 135° C., hence causing the external surface of the filament to melt and hence melt-bind to the vascular prosthesis wall.

While reducing the present invention to practice, it was uncovered that porosity increase in structures is obtained by heating the layer formed on precipitation electrode 22. In addition to its effect to the fiber structure porosity, the heating process reduces the amount of residual solvent and promotes better shape preservation while removing the final product from the mandrel, especially thin walled grafts. In accordance with the presently preferred embodiment of the invention, the heating process can be either external, for example, by lamps or differently-designed IR radiators, or applied internally by heating precipitation electrode 22, e.g. by Ohmic heaters. A typical heating temperature is between about 50° C. and about 100° C.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Materials, Devices and Methods

A silicon polycarbonate urethane copolymer CarboSil 20 was purchased from Polymer Technology Group Incorporated, and was used for graft manufacturing. This polymer has satisfactory fiber-generation abilities, it is biocompatibilty and is capable of lipophilic drug incorporation. A mixture of dimethylformamide and toluene of ratio ranging from 1:1 to 1:2 was used as a solvent in all experiments. For the formation of adhesive sublayers, polycarbonate urethane Chronoflex 80A was used.

A pump was purchased from Harvard Apparatus and was used in the electrospinning apparatus. For the dispensing electrode, three simultaneously operating spinnerets were used, mounted one above the other with a height of 20 mm therebetween. The inner diameter of the spinnerets was 0.5 mm. The flow-rate of each of the spinnerets was between 1 ml/h and 5 ml/h. The dispensing electrode was grounded while the precipitation electrode was kept at a potential of about 50 kV. The mandrel, made of polished stainless steel, was rotated at an angular velocity of 0.5–5 radians per second.

The dispensing electrode was positioned about 25 cm to 35 cm from the precipitation electrode and was connected to the pump with flexible polytetrafluorethylene tubes. Reciprocal motion of the dispensing electrode was enabled along the mandrel longitudinal axis at a frequency of 2÷3 motions/min. The longitudinal motion amplitude exceeded that of the manufactured graft by 10÷15%.

Example 1

A Two Layer Graft

A vascular prosthesis 6 mm in diameter and 200 mm in length was manufactured. A rod with 6 mm in diameter and 300 mm in length was used as a mandrel, and its central 200 mm portion was coated at ambient temperature, 24° C. Pump productivity was 3 ml/h.

CarboSil 20 polyuurethane solution was used to form both the inner layer and the outer layer, the thickness of which was 80 μm and 720 μm respectively, hence the total wall thickness was 800 μm. In the inner layer, the viscosity of the solution was 450 cP and the conductivity was 0.45 μS, and in the outer layer, the viscosity was 680 cP and the conductivity 1.8 μS. The graft was removed from the mandrel, rinsed repeatedly in deionized water, dried and sterilized.

Results

The mechanical parameters of the graft according to ISO 7198:1998 (E), were: general porosity of 68%, kinking diameter of 30 mm and dynamic compliance of 9%.

Example 2

The Effect of Solution Viscosity

A vascular prosthesis 6 mm in diameter and 200 mm in length was manufactured as described in Example 1, however for both inner layer and outer layer equal solution viscosity of 450 cP and equal conductivity of 0.45 µS was used. In addition, the pump productivity was increased to 5 ml/h.

Results

The above changes lead to a slightly higher value of general porosity but lower anti-kinking strength and compliance. The mechanical parameters of the graft according to the ISO were: general porosity of 70%, kinking diameter of 35 mm and dynamic compliance of 8%.

Example 3

The Effect of a Predetermined Fiber Orientation

A vascular prosthesis 6 mm in diameter and 200 mm in length was manufactured, as in Example 2, with the outer layer being formed from fibers placed in transverse (polar) orientation, for enhancing the radial strength of the graft. In addition, the thickness of the outer layer was 520 µm, hence total wall thickness reduced to 600 µm.

Results

The above changes lead to improvement of both antikinking resistance and dynamic compliance, without scarifying the general porosity. The mechanical parameters of the graft according to the ISO were: general porosity of 70%, kinking diameter of 32 mm and dynamic compliance of 10%.

Example 4

The Effect of Heating

A vascular prosthesis 6 mm in diameter and 200 mm in length was manufactured, as in Example 3, with the implementation of heating process as described herein. After the formation of the inner layer, an internal built-in Ohmic heater was employed so as to heat the mandrel and the inner layer to 70° C. The mandrel was kept in the above temperature throughout the process of outer layer formation.

Results

The heating of the mandrel after the formation of the inner layer resulted in a residual solvent drop from approximately 1200 ppm to 20 ppm. Low mass gain during the process ensured equal temperature of the mandrel and the outer layer. The heating process increased the porosity, the dynamic compliance and the antikinking resistance. The mechanical parameters of the graft according to the ISO were: general porosity of 78%, kinking diameter of 16 mm and dynamic compliance of 14%.

Example 5

The Effect of the Incorporation of a Coiled Pattern

A vascular prosthesis 6 mm in diameter and 200 mm in length was manufactured, as in Example 3, with an additional coiled pattern formed into the graft. The coiled pattern was formed by winding a 0.3-mm-thick RI CarboSil 20 filament, with a winding pitch of 1.1 mm, under a tension of 0.1 N. The winding process was started once the gross layer thickness had reached 500 µm, and the coiled pattern thickness was 100 µm.

Results

Reference is now made to FIG. 8, showing the reinforced graft. FIG. 8 demonstrates the reinforced graft antikinking resistance. The mechanical parameters of the graft according to the ISO are: general porosity of 64%, kinking diameter of 16 mm and dynamic compliance of 8%.

Example 6

A Multi Layer Graft with a an Additional Coiled Pattern

A vascular prosthesis 6 mm in diameter and 200 mm in length was manufactured. A rod 6 mm in diameter and a 300 mm in length was used as a mandrel, and its central 200 mm portion was coated at ambient temperature. Pump productivity was kept at 3 ml/h.

CarboSil 20 polyuurethane solution was used to form the inner layer, the thickness of which was 80 µm. The viscosity of the solution was 450 cP and conductivity was 0.45 µS. Once the inner layer was formed, a 16 µm first intermediate layer of low hardness, highly elastic polyurethane Chronoflex 80A was applied. Then, a 0.3 mm polypropylene surgical thread was passed through a bath of Chronoflex 80A solution of 1500 cP viscosity, thereby forming a semi-solid polyurethane filament with a thickness of about 1 mm. Subsequently, the coated filament was wound around the intermediate layer, at a winding rate of 4.4 m/min, winding tension of 2 N and winding pitch of 1.1 mm.

Once the winding process was completed, a second intermediate layer, identical to the first intermediate layer, was applied. An outer layer, of 720 µm thickness was applied using CarboSil 20 polyurethane solution having a viscosity of 680 cP and conductivity of 1.8 µS.

Results

As the thread was utterly coated, an adhesion bond sufficient to prevent uncoiling was formed. The mechanical parameters of the graft according to the ISO were: general porosity of 64%, kinking diameter of 12 mm and dynamic compliance of 5%.

Example 7

The Effect of Using a Polymer Fiber Extruder

A vascular prosthesis 6 mm in diameter and 200 mm in length was manufactured as in Example 6, except that a polymer filament extruder was used to generate the filament, and no dipping process was employed. CarboSil 20 was used as a melt for the polymer fiber extruder, and a perfectly rounded filament, 0.32 mm in diameter, was generated. The filament was initially generated at a temperature of 195° C. and was subsequently cooled by airflow, hence the filament contacted the graft at a temperature of 130° C., ensuring adhesion of the filament to the graft. In this example, the winding pitch was 1.4 mm.

Results

The polymer filament extruder improved the dynamical compliance of the graft, leaving the other parameters unchanged. Hence, the mechanical parameters of the graft according to the ISO were: general porosity of 64%, kinking diameter of 12 mm and dynamic compliance of 10%.

A summary of the mechanical parameters of the above Examples is provided in Table 1 and in FIG. 9, described below.

TABLE 1

| Example No. | 1 | 2 | 3 | 4 | 5 | 6 | 7 |
|---|---|---|---|---|---|---|---|
| Inner diameter [mm] | 6 | 6 | 6 | 6 | 6 | 6 | 6 |
| General porosity [%] | 68 | 70 | 70 | 78 | 64 | 64 | 64 |
| Kinking diameter [mm] | 30 | 35 | 32 | 16 | 16 | 12 | 12 |
| Dynamic compliance [%] | 9 | 8 | 10 | 14 | 8 | 5 | 10 |

Example 8

Ex-vivo Biological Properties

The present example is based on the cleavage of the tertazolium salt in the presence of an electron coupling reagents by active mitochondria producing a soluble formazan salt. Therefore, this conversion only occurs is viable cells.

Hence, cells grown in a 96 well tissue culture plate, were incubated with the salt mixture for 3 hours. Following the incubation period, the formazan dye formed is quantified using a scanning multiwell spectrofotometer, enabling a direct count of cell number.

Figure 9:
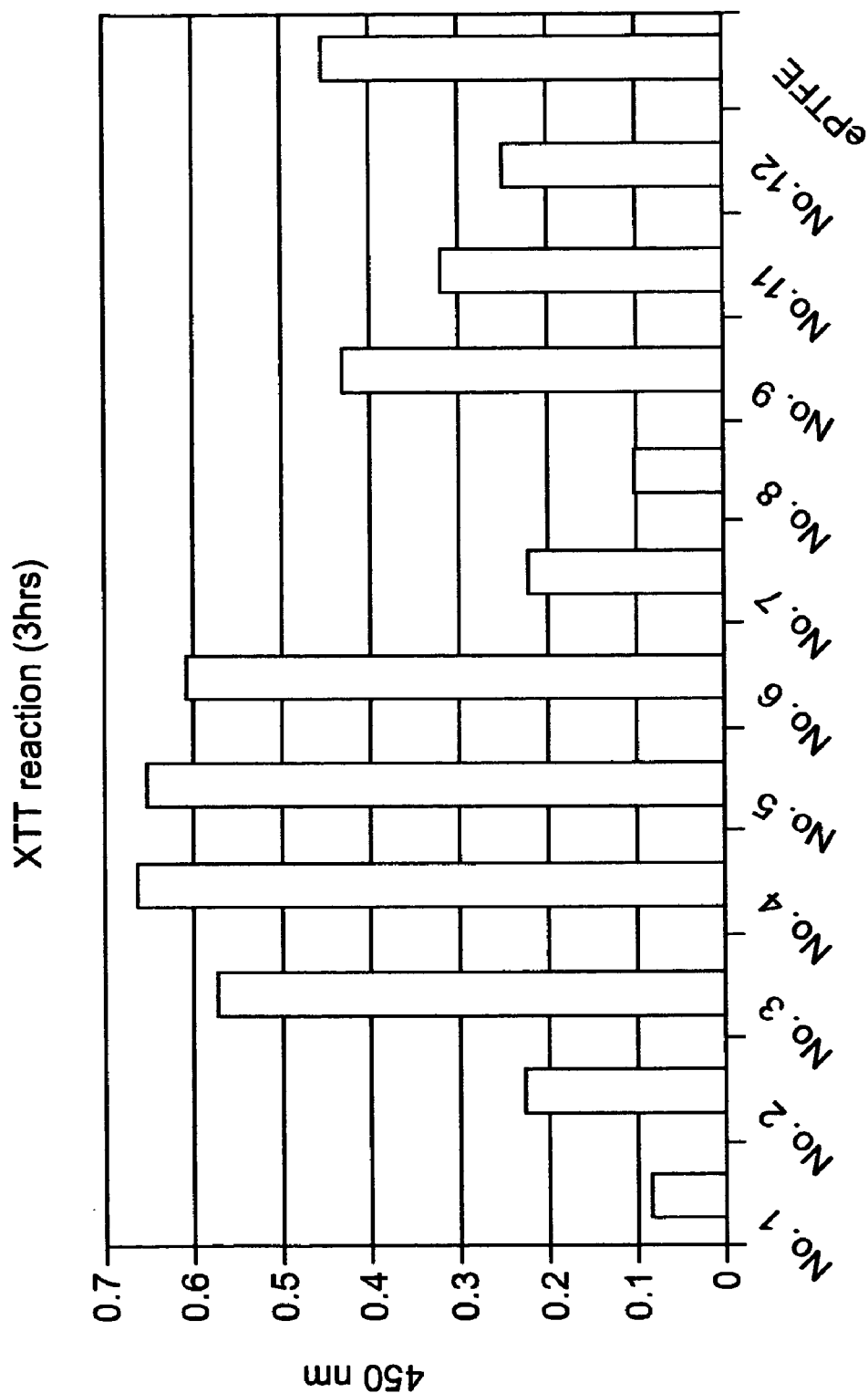
FIG. 9 is a plot of cell proliferation reaction efficiency versus type of the polymer support.

Reference is now made to FIG. 9 which is a graph representing the efficiency of the 3-hour cell proliferation reaction for various types of substrates.

In the graph, specimens Nos. 1 and 2 correspond to a first layer of thickness within 40–50 μm and about 65% porosity, formed from fibers having a diameter ranging from 40 nm to 60 nm.

Specimens Nos. 3–6 correspond to a first layer of thickness within 40–80 μm and about 50% porosity, formed from fibers having a diameter ranging from 50 nm to 150 nm.

Specimens Nos. 7 and 8 correspond to a first layer of thickness within 100–120 μm and about 60–80% porosity, formed from relatively coarse fibers having diameter of up to 1 μm.

The structures of specimens Nos. 9–12 are similar to those of specimens 3–6, with thickness of 120 μm for specimen 9, 20 μm for specimen 11, and 10 μm for specimen 12.

In addition, an ePTFE substrates, purchased from W. L. Gore Company, was used for comparison with all the above specimens.

Figure 10A:
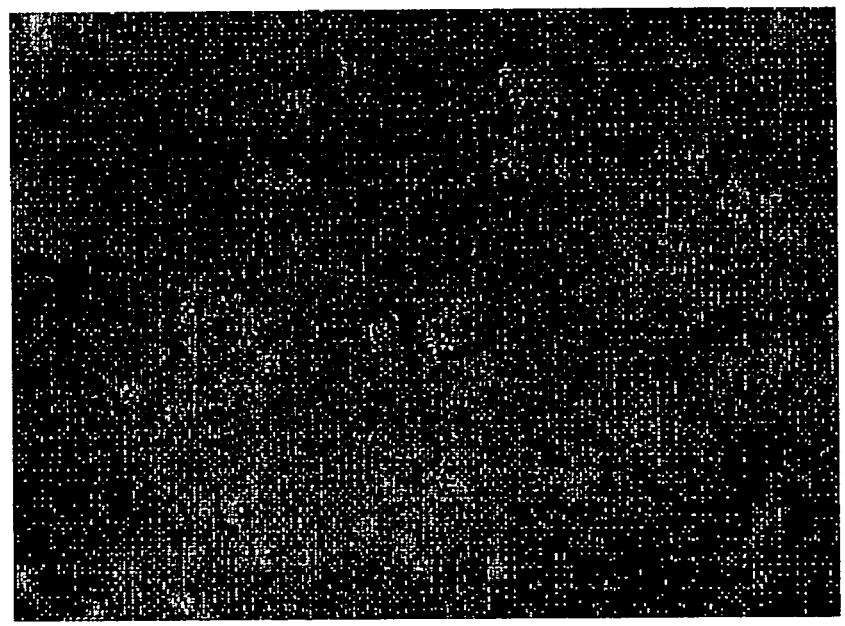
FIG. 10a is an electron microscope image of epithelial cells seeding, according to the teachings of the present invention.
Figure 10B:
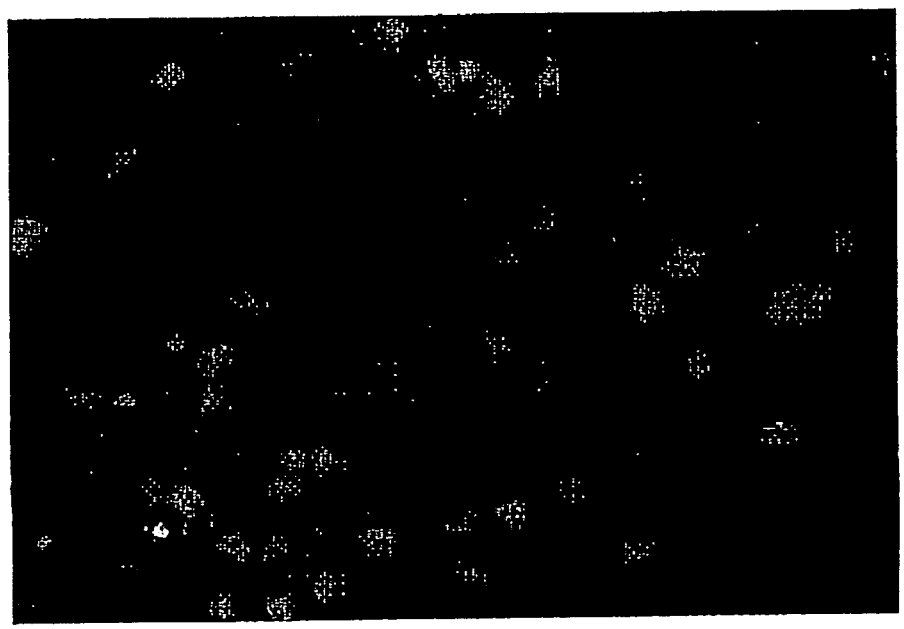
FIG. 10b is an electron microscope image of epithelial cells seeding, according to prior art teachings.

Reference made to FIGS. 10a–b, which is an electron microscopy image of epithelial cells adhered to a specimen 4 (FIG. 10a), compared to standard ePTFE substrates (FIG. 10b), purchased from W. L. Gore Company.

The advantage of the substrate of the present invention is evident from the large number of adhered epithelial cells evident in FIG. 10a, and the far smaller number of adhered epithelial cells evident in FIG. 10b.

Example 9

In vivo Biological Properties

A vascular graft, manufactured as described herein in Example 4, was implanted into a dog's femoral artery. The graft was removed for histological processing after 30 days after implantation.

Figure 11:
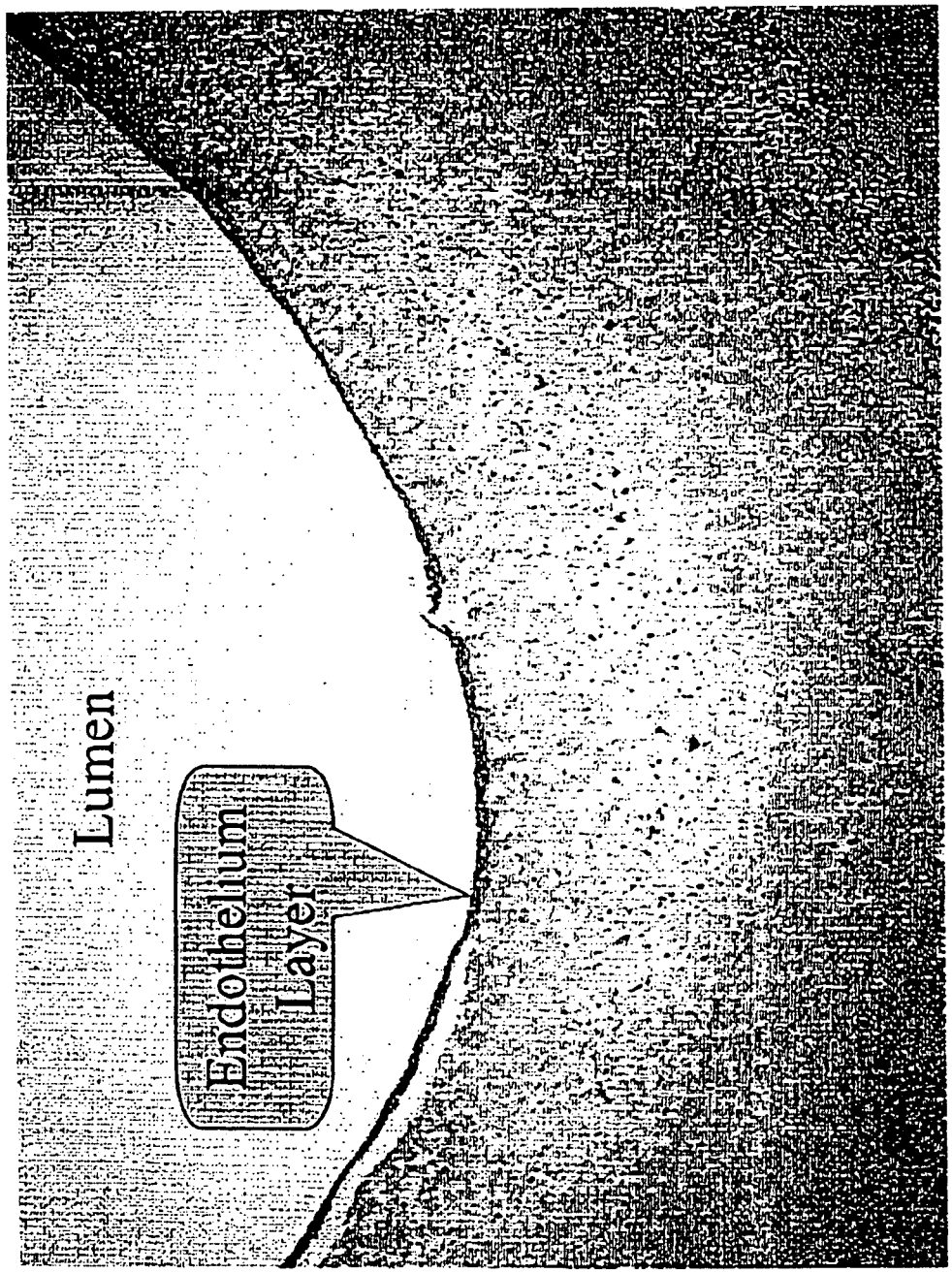
FIG. 11 shows results of histological investigations.

Reference now made to FIG. 11, which shows a histological section of the vascular graft. As can be seen, the inner surface of the graft was lined by endothelium. The endothelium was migrating along an irregular thin tissue layer, which lined the inner surface of the graft. The layer had all the components of an organizing thrombus.

The graft inner layer plays important role in ensuring general prosthesis patency. Immediately after implantation, a nanofiber layer, with a dense structure having a smooth and concomitantly an elastic surface, contacts with blood flow and prevents bleeding and thrombopoiesis. Within the following two to three weeks, the layer properties ensure efficient endothelization.

Example 10

In vivo Biological Properties

A vascular graft, manufactured as described herein in Example 4, was implanted into a dog's right leg artery. For comparison, an ePTFE graft have been implanted into the dog's left leg artery. The implanted grafts have been imaged, 6 weeks after implantation.

Figure 12B:
FIG. 12b shows results of angiographia of a graft, according to prior art teachings.
Figure 12A:
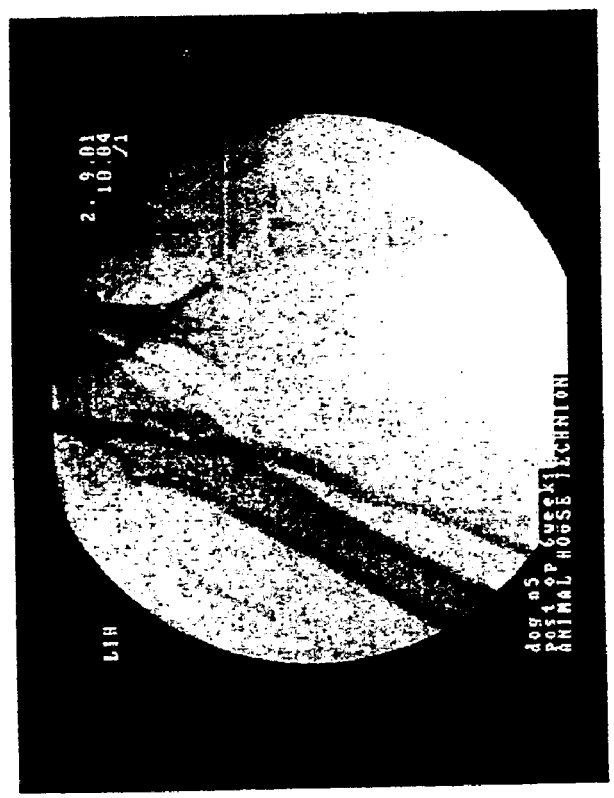
FIG. 12a shows results of angiographia of a graft, according to the teachings of the present invention.

Reference now made to FIGS. 12a–b, and 13a(i)–13b(iv) which show, angiograph images and IVUS images of the implanted grafts, respectively. FIG. 12a shows an angiograph image of the vascular graft, manufactured according to the present invention, and FIG. 12b shows an angiograph image of the ePTFE graft. In FIG. 12a, no narrowing or thrombus occlusion is shown and the lumen is open through its length. In FIG. 12b, at the proximal connection of the ePTFE graft, a narrowing of the graft and/or thrombus occlusion of approximately 30–50% is shown.

Referring to FIGS. 13a–b, four IVUS images are shown at the lumen of each graft from the proximal connection to the distal connection. These images are marked R1 to R4 for the graft of the present invention, and L1 to L4 for the ePTFE graft. A narrowing of the lumen is vivid at the ePTFE graft, whereas the lumen of the graft, manufactured according to the present invention, is open.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of producing a vascular prosthesis, the method comprising:

electrospinning a first liquefied polymer onto a precipitation electrode hence providing a first layer having a predetermined first porosity;

electrospinning a second liquefied polymer onto said precipitation electrode hence providing a second layer having a predetermined second porosity being larger than said predetermined first porosity; and electrospinning at least one additional liquefied polymer onto said precipitation electrode prior to the step of electrospinning the second liquefied polymer, hence providing at least one intermediate layer interposed between said first layer and said second layer.

2. The method of claim 1, wherein said precipitation electrode is a rotating mandrel.

3. The method of claim 1, wherein each of said electrospinning steps comprising:
(a) charging said liquefied polymer thereby producing a charged liquefied polymer;
(b) subjecting said charged liquefied polymer to a first electric field; and
(c) dispensing said charged liquefied polymers within said first electric field in a direction of said precipitation electrode.

4. The method of claim 3, further comprising providing a second electric field defined by a subsidiary electrode being at a second potential relative to said precipitation electrode, said second electric field being for modifying said first electric field.

5. A method of producing a vascular prosthesis, the method comprising:
electrospinning a first liquefied polymer onto a precipitation electrode hence providing a first layer having a predetermined first porosity;
electrospinning a second liquefied polymer onto said precipitation electrode hence providing a second layer having a predetermined second porosity;
electrospinning at least one additional liquefied polymer onto said precipitation electrode prior to the step of electrospinning the second liquefied polymer, hence providing at least one intermediate layer interposed between said first layer and said second layer; and
winding a filament around at least one of said first layer, said second layer, and at least one of said at least one intermediate layer hence providing at least one layer which comprises at least one coiled pattern.

6. The method of claim 5, wherein said step of winding and at least one of said steps of electrospinning are performed simultaneously.

7. The method of claim 5, further comprising coating said filament by a polyurethane solution prior to said step of winding said filament.

8. The method of claim 3, wherein said first electric field is defined between said precipitation electrode and a dispensing electrode being at a first potential relative to said precipitation electrode.

9. The method of claim 4, wherein said subsidiary electrode serves for reducing non-uniformities in said first electric field.

10. The method of claim 4, wherein said subsidiary electrode serves for controlling fiber orientation of said polymer fiber shell generated upon said precipitation electrode.

11. The method of claim 1, wherein said first layer is an inner layer and said second layer is an outer layer.

12. The method of claim 1, wherein each of said first layer and said second layer is independently of a tubular structure.

13. The method of claim 5, wherein said filament is formed by polymer fiber extruder.

14. The method of claim 13, wherein said polymer filament extruder includes a bath for holding a melted polymer.

15. The method of claim 14, wherein said melted polymer is a biocompatible melted polymer.

16. The method of claim 15, wherein at least a portion of said biocompatible melted polymer includes a melted polyurethane.

17. The method of claim 13, further comprising cooling said filament by airflow upon exiting said polymer fiber extruder.

18. The method of claim 7, wherein said coating comprises dipping said filament into said polyurethane solution.

19. The method of claim 5, further comprising heating said filament prior to, during or subsequent to said step of winding said filament.

20. A method of producing a vascular prosthesis, the method comprising:
electrospinning a first liquefied polymer onto a rotating mandrel hence providing a first layer having a predetermined first porosity;
electrospinning a second liquefied polymer onto said rotating mandrel hence providing a second layer having a predetermined second porosity; and
electrospinning at least one additional liquefied polymer onto said rotating mandrel prior to the step of electrospinning the second liquefied polymer, hence providing at least one intermediate layer interposed between said first layer and said second layer;
wherein the method further comprising heating said mandrel prior to, during or subsequent to said step of electrospinning.

21. The method of claim 20, wherein said heating of said mandrel is selected from the group consisting of external heating and internal heating.

22. The method of claim 21, wherein said external heating is by at least one infrared radiator.

23. The method of claim 21, wherein said at least one infrared radiator is an infrared lamp.

24. The method of claim 21, wherein said internal heating is by a built-in heater.

25. The method of claim 24, wherein said built-in heater is an Ohmic built-in heater.

26. The method of claim 5, wherein said filament is selected from the group consisting of a polypropylene filament and a polyurethane filament.

27. The method of claim 5, wherein said filament has a cross-section selected from the group consisting of a circular cross section, an ellipsoid cross section a polygonal cross section and an irregular pattern cross section.

28. The method of claim 5, wherein said at least one intermediate layer includes a plurality of adhesion sublayers, alternately interposed between said first layer and said coiled pattern, between said coiled pattern and said second layer, and between two congruent coiled patterns.

29. The method claim 28, wherein said adhesion sublayers are impervious adhesion sublayers.

30. The method of claim 28, wherein said adhesion sublayers are formed from electrospun polymer fibers.

31. The method of claim 1, wherein said at least one intermediate layer has a predetermined porosity.

32. The method of claim 1, wherein each of said first liquefied polymer and said second liquefied polymer are independently biocompatible.

33. The method of claim 1, wherein each of said first liquefied polymer, said second liquefied polymer and said at least one additional liquefied polymer are independently biocompatible.

34. The method of claim 1, wherein each of said first liquefied polymer, said second liquefied polymer and said at least one additional liquefied polymer is independently selected from the group consisting of polyethylene terephtalat fibers and polyurethane fibers.

35. A method of producing a vascular prosthesis, the method comprising:
electrospinning a first liquefied polymer onto a precipitation electrode hence providing a first layer having a predetermined first porosity;

electrospinning a second liquefied polymer onto said precipitation electrode hence providing a second layer having a predetermined second porosity;

electrospinning at least one additional liquefied polymer onto said precipitation electrode prior to the step of electrospinning the second liquefied polymer, hence providing at least one intermediate layer interposed between said first layer and said second layer; and incorporating at least one drug within at least one of said first liquefied polymer, said second liquefied polymer and said at least one additional liquefied polymer, for delivery of said at least one drug into a body vasculature during or after implantation of the vascular prosthesis within said body vasculature;

wherein each of said first liquefied polymer, said second liquefied polymer and said at least one additional liquefied polymer are independently combination of a biodegradable liquefied polymer and a biostable liquefied polymer.

* * * * *